United States Patent [19]

Ord, Jr.

[11] 4,331,025
[45] May 25, 1982

[54] METHODS OF MEASURING FLUID VISCOSITY AND FLOW RATE

[75] Inventor: Robinson Ord, Jr., Tulsa, Okla.

[73] Assignee: Mapco, Inc., Tulsa, Okla.

[21] Appl. No.: 196,634

[22] Filed: Oct. 14, 1980

[51] Int. Cl.³ .................... G01F 1/66; G01N 29/02
[52] U.S. Cl. ................................ 73/54; 73/597; 73/861.02; 73/861.28
[58] Field of Search ............ 73/53, 54, 597, 861.02, 73/861.03, 861.27, 861.28

[56] References Cited

U.S. PATENT DOCUMENTS

| | | | |
|---|---|---|---|
| 3,290,934 | 12/1966 | Brown et al. | 73/24 X |
| 3,512,394 | 5/1970 | Kleiss | 73/54 |
| 4,015,470 | 4/1977 | Morrison | 73/861.03 |
| 4,080,837 | 3/1978 | Alexander et al. | 73/597 X |
| 4,300,400 | 11/1981 | Bistrian, Jr. et al. | 73/861.28 |

OTHER PUBLICATIONS

Lynch et al., "Flow Measurement with a New Ultrasonic Flowmeter" *Flow, its Measurement and Control in Science and Industry*, vol. 1, Part II, 1974.

*Primary Examiner*—Charles A. Ruehl
*Attorney, Agent, or Firm*—Head & Johnson

[57] ABSTRACT

A method of measuring the flow rate of a fluid through a conduit by means of a sonic flow meter employing the steps of measuring the speed of sound transmission through the fluid from an upstream point in the conduit to an opposed downstream point, measuring the speed of sound transmission through the fluid from the downstream point to the upstream point, subtracting the two measurements to obtain a liquid flow rate indication, adding the two measurements to obtain the fluid sound velocity, measuring the temperature of the fluid in the conduit, determining a measurement of the fluid viscosity from the fluid speed of sound transmission and the temperature, and correcting the determined fluid velocity utilizing the detected fluid viscosity.

6 Claims, 2 Drawing Figures

METHODS OF MEASURING FLUID VISCOSITY AND FLOW RATE

BACKGROUND OF THE INVENTION

1. Field of the Invention

This invention relates to the field of sonic flow meters of the type particularly described as ultrasonic, single-path, transit time flow meters such as described in U.S. Pat. No. 3,720,105. The invention is particularly directed to the field of ultrasonic flow meters having computational apparatus for correcting sonically determined flow rates for viscosity, to provide corrected flow rates.

2. Description of the Prior Art

A convenient and commonly used means of measuring liquid flow is by the use of sonic flow meters. These are devices which transmit sound pulses through the fluid flowing in a conduit. In the most commonly practiced means of employing ultrasonics for measuring fluid flow rate, a sonic path is provided between an upstream and downstream location spaced on opposite sides of a conduit. In the preferred method of practicing the invention the rate of travel of the sound through the liquid is measured in both directions, that is, with the fluid flow component and against the fluid flow component. By subtracting such measurements, which effectively cancels out the rate of sound travel through the fluid itself, the rate of the fluid flow can be accurately determined.

The application of ultrasonic flow meters to measurement of such products as water which change little in viscosity, has been successfully employed. Difficulty, however, is experienced in the use of ultrasonic flow meters to measure volumetric flow rates of fluids which vary considerably in viscosity. This is particularly a problem in attempts to utilize ultrasonic flow meters in the petroleum industry wherein the viscosity of the hydrocarbon fluids varies over a great range.

An object of the present invention is to provide means of utilizing ultrasonic flow meters for measuring the flow rates of fluids having variable viscosities.

Another object of this invention is to provide means employing sonic measurements to determine the viscosity of a fluid flowing in a conduit.

Another object of this invention is to provide means employing empirically derived relationships for calculating corrected flow rates of fluids wherein the measurements required for determining the flow rate are supplied as upstream and downstream sonic measurements along with the fluid temperature measurement.

These general objects as well as other and more specific objects of the invention will be fulfilled in the following description and claims, taken in conjunction with the attached drawings.

SUMMARY OF THE INVENTION

A method is provided for measuring the flow rate V of a fluid through a conduit having an inside dimensional constant D and a fluid temperature T employing an ultrasonic flow meter. The method is accomplished by measuring the speed of sound transmission through the liquid from a downstream point in the conduit to an opposed upstream point separated by a sonic path length L to provide a value $f_A$. Next, the speed of sound transmission is measured through the fluid in the opposite direction, that is, from the upstream point to the downstream point to provide a value $f_B$. By adding $f_A$ to $f_B$, a value C is obtained which is indicative of the fluid sound velocity. A corrected fluid sound velocity C' is obtained by the formula $$[L(f_A+f_B)]/2N$$

where N is a multiplier factor. Subtracting $f_A$ from $f_B$ provides a value V from which the fluid velocity V' can be calculated. The kinematic viscosity $V_k$ of the fluid is calculated utilizing values C' and T and an empirically derived algorithm. The Reynolds number $R_e$ of the fluid is calculated by the formula $DV/V_k$ and a constant $K_2$ is derived from the Reynolds number employing an empirically determined relationship. A constant $K_1$ is derived for the formula $2ND/L^2$. The uncorrected fluid flow velocity V' is derived from $V/K_1$, the corrected flow rate V'' by the formula $V'/K_2$.

DETAILED DESCRIPTION OF THE PREFERRED EMBODIMENT

Figure 1:
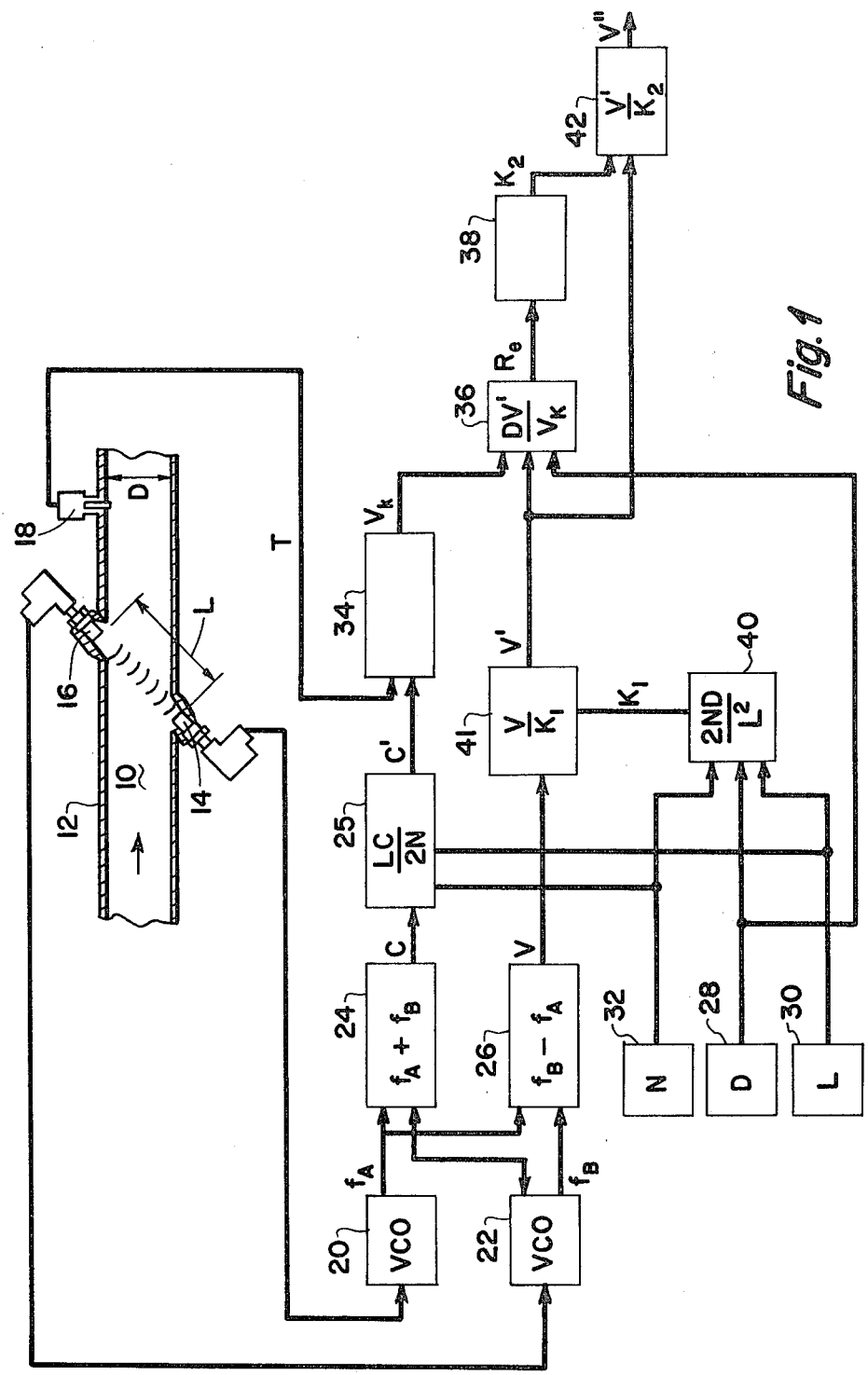
FIG. 1 is a block diagram of the components employed in the invention and showing diagrammatically the measurement of sound along a sonic path in a conduit.

In the drawing and the specification the following nomenclature is employed:

VCO = Voltage Controlled Oscillator
$f_A$ = Upstream VCO frequency
$f_B$ = Downstream VCO frequency
T = Liquid Temperature
C = Velocity of sound in the liquid as indicated by a sum of $f_A$ and $f_B$.
C' = Velocity of sound in the liquid corrected for the parameters by which $f_A$ and $f_B$ are measured.
V = Velocity of the fluid as indicated by $f_B - f_A$.
V' = Velocity of the fluid corrected for the parameters by which $f_A$ and $f_B$ are measured.
V'' = Velocity of the fluid corrected for variations in fluid velocity and viscosity.
D = Dimensional constant derived from the conduit cross-sectional shape and size and the angle of acoustic transmission direction with respect to the conduit axis. For a circular conduit and a 45° angle of acoustic transmission, D is equal to the inside diameter of the conduit.
L = Length of the sonic path
$R_e$ = Reynolds number
$K_1$ = Constant used to correct the sonic meter measurement V into units of flow based on physical conditions.
$K_2$ = Constant used to correct the sonic meter measurement V' for fluid velocity and viscosity.

Referring to the drawings, the basic apparatus for practicing the invention is illustrated in block diagram and schematic form in FIG. 1. The object of the invention is to determine the flow rate of the fluid 10 flowing through conduit 12. The invention is particularly directed towards such measurement when the fluid 10 is of the type having variable viscosity, such as hydrocarbon fluids. Positioned in conduit 12 is a first, upstream, sonic energy transmitting and receiving station 14. A second sonic transmitting and receiving station 16 is placed downstream of station 14 and on the opposite side of conduit 10 from station 14. Between stations 14 and 16 a sonic path of length L is established.

The apparatus including sonic stations 14 and 16 is well known and is of the type commonly employed in sonic flow meters, and for more information as to the structure and operation of such devices, reference may be made to U.S. Pat. No. 3,720,105.

Affixed to conduit 12 is a temperature measuring device 18 by which the temperature T of the fluid 10 is detected.

While various means may be employed for transmitting and receiving sound pulses between stations 14 and 16, a commonly employed arrangement is the use of voltage controlled oscillators (VCO) 20 and 22. A measure of the speed of sound transmission along the path L between the second sonic station 16 and the first sonic station 14 is given by voltage controlled oscillator 20 which provides a signal output indicated by $f_A$, that is, the upstream voltage controlled oscillator frequency. In like manner, a measure of the speed of sound transmission between upstream station 14 and downstream station 16 is provided by voltage controlled oscillator 22 which provides an output $f_B$ representative of the downstream voltage controlled oscillator frequency. The signal $f_A$ is proportional to the speed of sound transmission through liquid 10 from downstream point 16 in the conduit to the opposed upstream point 14. The signal at $f_B$ is proportional to the speed of sound transmission through the fluid 10 from the upstream point 14 to the downstream point 16. The signals $f_A$ and $f_B$ are added in the circuit 24 providing, at the output, a signal C which is indicative of the fluid sound velocity, that is, the speed of travel of sound in the fluid irrespective of the direction or speed of movement of the fluid. The signal C is treated in circuit 25 to correct for the physical parameter of measurement by the formulae LC/2N, to provide the corrected sound velocity signal C'. By subtracting $f_A$ from $f_B$ in subtraction circuit 26 a signal V is provided which is dependent on the fluid flow velocity. In effect, the subtraction circuit 26 cancels the effect of the speed of sound transmission of the fluid itself leaving only the component attributable to the movement of fluid 10 through conduit 12 and points 14 and 16.

In the computational circuitry of FIG. 1, process constants are inserted. D is a constant representative of size and dimensions of conduit 12 and the angle of the sonic flow path. L is the sonic path length between points 14 and 16. These values may be inserted into the circuitry, either in analog or digital form, by the circuitry components 28 and 30. An additional process constant is a multiplier factor N which is typically selected as a function of sound velocity C and transducer spacing L to yield the largest possible values for $f_A$ and $f_B$ within the limitations of VCO's 20 and 22. This corrective multiplier is placed into the circuitry utilizing component 32.

An important aspect of the invention is the method by which the kinematic viscosity of the liquid 10 may be determined and the use of the determined kinematic viscosity in correcting the flow velocity to provide a viscosity corrected fluid flow rate measurement.

Circuitry 34, which may be in the form of a programmed computer chip using an empirically derived algorithm, is employed for computing the kinematic viscosity of the liquid. The input into circuitry 34 is the sound velocity C' of the fluid and the temperature T. It has been unexpectedly discovered that fluid kinematic viscosity is relatively linear on a logarithmic scale as a function of the speed of sound transmission of the fluid and of the temperature. It has been determined that when the fluid 10 is a hydrocarbon type liquid, such as crude oil, gasoline, propane, diesel fuel, etc. an algorithm employed in circuitry 34 may take the following form:

$$V_k = 10^{(K_3 + 10(K_4 + K_5 T + K_6 C'))}$$

where $K_3$, $K_4$, $K_5$ and $K_6$ are empirically determined constants, the values of which depend on the nature of the fluids to be metered and units employed in $V_k$, T, and C'.

A commonly employed method of correcting a flow meter of the sonic type employs the Reynolds number of the liquid. This may be obtained in circuitry 36 using the formula $DV'/V_k$. That is, the Reynolds number is the ratio of the measured flow rate divided by the kinematic viscosity of the fluid. Since the flow of fluid through a conduit is not at the same rate at all distances from the inside wall of the conduit due to the drag imposed by the conduit walls, a constant is required to reflect the average velocity along the line between the sonic transducers at points 14 and 16 versus the average velocity of the fluid in the cross-section of the conduit. This is the constant $K_2$ and is obtained from the Reynolds number $R_e$. This information in the calibration of a meter reading is normally taken from a chart supplied with each sonic flow meter model.

Figure 2:
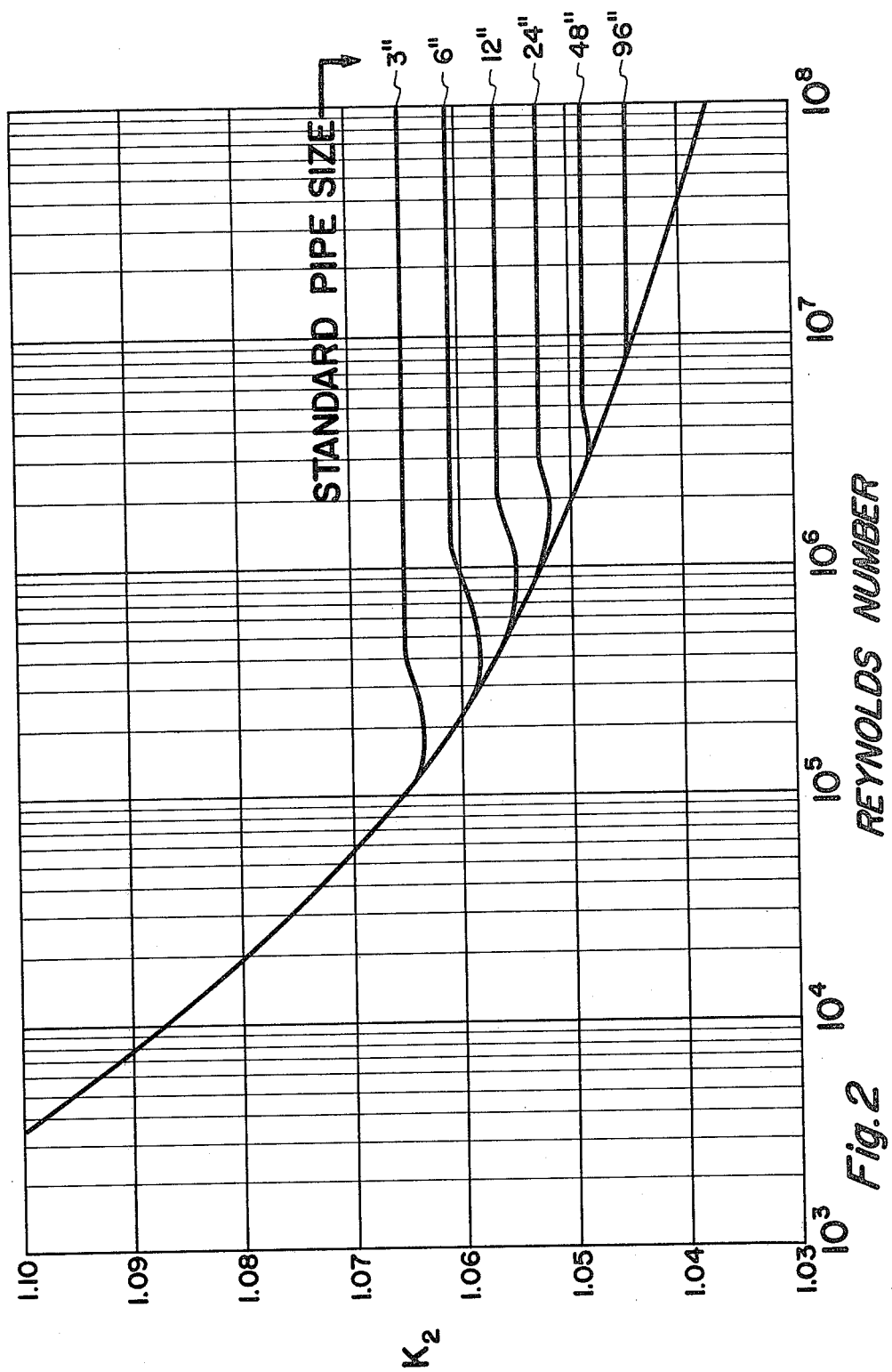
FIG. 2 is a logarithmic graph showing the typical relationship between the constant $K_2$ and the Reynolds number for a variety of standard pipe sizes.

FIG. 2 shows a typical empirically derived chart for a sonic flow meter wherein the constant $K_2$ is the ordinate and the Reynolds number $R_e$ is the abscissa. This chart has been plotted for a sonic flow meter where conduit 12 is a standard pipe size with calibrations made for pipes of 3", 6", 12", 24", 48", and 96" nominal pipe size. For each sonic meter the computational circuitry of element 38 provides the correct output $K_2$ for the Reynolds number input.

To correct the measured flow rate signal V for the physical parameters employed in the measurement, a constant $K_1$ is required. This constant is obtained in circuitry 40 by the formula $2ND/L^2$.

Circuit 41 corrects the detected flow velocity V by the formula $V/K_1$ to obtain V'. The value V' is fed to circuit 36 for use in calculating the Reynolds number $R_e$ as previously described, and in addition, is fed to circuit 42 where the fluid velocity V' is corrected by the formula $V'/K_2$ to obtain the final fluid velocity V" which is fully corrected for physical measurement parameters and fluid viscosity.

All of the circuitry required can be accomplished using state of the art technology and microcomputer processes which are not a part of the present invention since they are well within the skill of the art.

The invention has been described and illustrated based on the assumption that conduit 12 has a circular internal cross-section. While this is the typical environment in which sonic flow meters are employed, it can be seen that the same principles of the invention are applicable to conduits 12 having square, rectangular, elliptical, or any other shape cross-section.

While the invention has been described with a great degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of measuring the flow rate of a fluid through a conduit comprising:
    (a) measuring the speed of sound transmission through the fluid from an upstream point in the conduit to an opposed downstream point;
    (b) measuring the speed of sound transmission through the fluid from said downstream point to said upstream point;
    (c) subtracting the measurement of step (b) from the measurement of step (a) to determine the fluid flow rate;
    (d) adding the measurement of step (a) to the measurement of step (b) to determine the fluid sound velocity;
    (e) measuring the temperature of the fluid in the conduit;
    (f) determining a fluid viscosity factor from the measured fluid sound velocity and temperature; and
    (g) correcting the fluid flow rate by the fluid viscosity factor to obtain a corrected fluid flow rate.

2. A method of determining the viscosity of a fluid comprising:
    (a) measuring the speed of sound transmission of the fluid;
    (b) measuring the temperature of the fluid; and
    (c) calculating the fluid viscosity by employing an empirical formula in which the variables are the fluid speed of sound transmission derived from step (a) and the fluid temperature derived from step (b).

3. A method of determining the viscosity of a liquid according to claim 2 wherein the fluid is flowing through a conduit and the step of determining the speed of sound transmission of the fluid comprises:
    (d) measuring the speed of sound transmission of the fluid from an upstream point to an opposed downstream point;
    (e) measuring the speed of sound transmission of the fluid from the downstream point to the upstream point; and
    (f) adding the measurement of step (d) to the measurement of step (e).

4. A method of determining the viscosity of a liquid according to claim 2 wherein said formula employed in step (c) is $$V_k = 10^{(K_3 + 10(K_4 + K_5 T + K_6 C'))}$$

where $V_k$ is kinematic viscosity, T is fluid temperature, $C'$ is the liquid sound velocity, and $K_3$, $K_4$, $K_5$, and $K_6$ are empirically derived constants for each type of fluid being measured.

5. A method of measuring the volumetric flow rate of a liquid through a conduit comprising the steps of:
    (a) measuring the speed of sound transmission through the liquid from a downstream point in the conduit to an opposed upstream point separated by a sonic path length L to provide a value $f_A$;
    (b) measuring the speed of sound transmission through the liquid from said upstream point to said downstream point to provide a value $f_B$;
    (c) adding $f_A$ to $f_B$ to provide a value C indicative of the fluid sound velocity;
    (d) subtracting $f_A$ from $f_B$ to provide a value V indicative of the fluid flow velocity;
    (e) deriving the actual velocity of sound $C'$, correcting C for the parameters by which $f_A$ and $f_B$ are measured, by the formula LC/2N where N is a multiplier selected according to C and L;
    (f) measuring the temperature T of the fluid;
    (g) calculating the kinematic viscosity $V_k$ of the fluid utilizing the values $C'$ and T using an empirically derived algorithm;
    (h) deriving a constant $K_1$ by the formula $2ND/L^2$ where N is a multiplier factor selected according to $C'$ and L, and D is a constant determined by the physical parameters of the conduit and the second paths;
    (i) correcting the fluid velocity V to obtain $V'$ by the formula $V' = V/K_1$;
    (j) calculating the Reynolds number $R_e$ for the fluid by the formula $DV'/V_k$;
    (k) deriving a constant $K_2$ from $R_e$ employing an empirically determined relationship, and
    (l) calculating the corrected fluid velocity $V''$ by the formula $V'/K_2$.

6. The method of measuring the volumetric flow rate of a liquid as in claim 5 wherein the algorithm employed in step (g) to compute the kinematic viscosity of the liquid is:

$$V_k = 10^{(K_3 + 10(K_4 + K_5 T + K_6 C'))}$$

where $V_k$ is kinematic viscosity, T is fluid temperature, $C'$ is the liquid sound velocity, and $K_3$, $K_4$, $K_5$, and $K_6$ are empirically derived constants for each type of fluid being measured.

* * * * *

UNITED STATES PATENT AND TRADEMARK OFFICE
CERTIFICATE OF CORRECTION

PATENT NO. : 4,331,025
DATED : May 25, 1982
INVENTOR(S) : Robinson Ord, Jr.

It is certified that error appears in the above-identified patent and that said Letters Patent are hereby corrected as shown below:

Column 2, line 12, change $DV/V_k$ to -- $DV'/V_k$ --

Column 4, line 10, change $V_k = 10^{(K_3 + 10(K_4+K_5T+K_6C))}$ to $V_k = 10^{(K_3 + 10^{(K_4+K_5T+K_6 C')})}$ Column 6, line 1, change $V_k = 10^{(K_3+10\ (K_4+K_5T+K_6C))}$ to $V_k = 10^{(K_3+10^{(K_4+K_5T+K_6 C')})}$ Column 6, line 32, change "second" to --sound--

Column 6, line 46, change $V_k = 10^{(K_3+10(K_4+K_5T+K_6C))}$ to $V_k = 10^{(K_3+ 10^{(K_4+K_5T+K_6 C')})}$ Signed and Sealed this Fifth Day of October 1982

[SEAL]

Attest:

GERALD J. MOSSINGHOFF

Attesting Officer   Commissioner of Patents and Trademarks